United States Patent [19]

Wyman

[11] Patent Number: 5,157,160
[45] Date of Patent: Oct. 20, 1992

[54] CERTAIN 5-SUBSTITUTED-1-AZABICYCLO[3.1.1]HEPTANES AND THEIR PHARMACEUTICAL USE

[75] Inventor: Paul A. Wyman, Harlow, England

[73] Assignee: Beecham Group p.l.c., Brentford, England

[21] Appl. No.: 716,213

[22] Filed: Jun. 17, 1991

Related U.S. Application Data

[62] Division of Ser. No. 566,980, Aug. 14, 1990, Pat. No. 5,043,343.

[30] Foreign Application Priority Data

Aug. 16, 1989 [GB] United Kingdom ............... 8918658
Aug. 16, 1989 [GB] United Kingdom ............... 8918659
Feb. 28, 1990 [GB] United Kingdom ............... 9004437

[51] Int. Cl.$^5$ .............................................. C07D 471/08
[52] U.S. Cl. .................................................. 546/112
[58] Field of Search ....................................... 546/112

[56] References Cited

U.S. PATENT DOCUMENTS 4,971,975 11/1990 Hadley et al. ................. 546/112

*Primary Examiner*—Bernard Dentz
*Attorney, Agent, or Firm*—Hopgood, Calimafde, Kalil, Blaustein & Judlowe

[57] ABSTRACT

A compound of formula (I) or a pharmaceutically acceptable salt thereof:

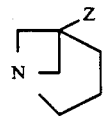

(I)

in which Z is a heterocyclic group

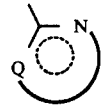

in which Q represents a 3-membered divalent residue completing a 5-membered aromatic ring and comprises one or two heteroatoms selected from oxygen, nitrogen and sulphur, or three nitrogen atoms, any amino nitrogen being substituted by a $C_{1-2}$ alkyl, cyclopropyl or propargyl group, and any ring carbon atom being optionally substituted by a group $R_1$; or a group

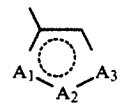

in which $A_1$, $A_2$ and $A_3$ complete a 5-membered aromatic ring and $A_1$ is oxygen or sulphur, one of $A_2$ and $A_3$ is $CR_2$ and the other is nitrogen or $CR_3$, or $A_2$ is oxygen or sulphur, one of $A_1$ and $A_3$ is $CR_2$ and the other is $CR_3$; and $R_1$, $R_2$ and $R_3$ are independently selected from hydrogen, halogen, CN, $OR_4$, $SR_4$, $N(R_4)_2$, $NHCOR_4$, $NHCOOCH_3$, $NHCOOC_2H_5$, $NHOR_4$, $NHNH_2$, $NO_2$, $COR_4$, $COR_5$, cyclopropyl, $C_{2-5}$ straight chain alkenyl, $C_{2-5}$ straight chain alkynyl or $C_{1-5}$ straight chain alkyl optionally terminally substituted with $OR_4$, $N(R_4)_2$, $SR_4$, $CO_2R_4$, $CON(R_4)_2$ or one, two or three halogen atoms, in which each $R_4$ is independently hydrogen or $C_{1-3}$ alkyl and $R_5$ is $OR_4$, $NH_2$ or $NHR_4$; or in which Z is a group —$C(R_7)$=$NR_6$ in which $R_6$ is a group $OR_8$, where $R_8$ is $C_{1-4}$ alkyl, $C_{2-4}$ alkenyl, $C_{2-4}$ alkynyl, a group $OCOR_9$ where $R_9$ is hydrogen or $R_8$, or a group $NHR_{10}$ or $NR_{11}R_{12}$ where $R_{10}$, $R_{11}$ and $R_{12}$ are independently $C_{1-2}$ alkyl and $R_7$ is hydrogen or $C_{1-4}$ alkyl, subject to the proviso that when $R_6$ is a group $OCOR_9$ or $NHR_{10}$, $R_7$ is $C_{1-4}$ alkyl. The compounds are potentially useful in the treatment of diseases of the nervous system.

3 Claims, No Drawings

CERTAIN 5-SUBSTITUTED-1-AZABICYCLO[3.1.1]HEPTANES AND THEIR PHARMACEUTICAL USE

This is a division of copending application Ser. No. 566,980, filed Aug. 14, 1990, now U.S. Pat. No. 5,043,343.

This invention relates to compounds having pharmaceutical activity, to a process for their preparation and their use as pharmaceuticals.

EP-A-0287356 discloses certain substituted 1-azabicyclic compounds which enhance acetylcholine function via an action at muscarinic receptors within the central nervous system.

A novel group of compounds has been discovered which also enhance acetylcholine function via an action at muscarinic receptors within the central nervous system and are therefore of potential use in the treatment and/or prophylaxis of dementia in mammals.

According to the present invention, there is provided a compound of formula (I) or a pharmaceutically acceptable salt thereof:

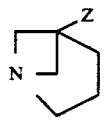
(I)

in which Z is a heterocyclic group

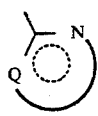

in which Q represents a 3-membered divalent residue completing a 5-membered aromatic ring and comprises one or two heteroatoms selected from oxygen, nitrogen and sulphur, or three nitrogen atoms, any amino nitrogen being substituted by a $C_{1-2}$ alkyl, cyclopropyl or propargyl group, and any ring carbon atom being optionally substituted by a group $R_1$; or a group

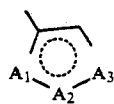

in which $A_1$, $A_2$ and $A_3$ complete a 5-membered aromatic ring and $A_1$ is oxygen or sulphur, one of $A_2$ and $A_3$ is $CR_2$ and the other is nitrogen or $CR_3$, or $A_2$ is oxygen or sulphur, one of $A_1$ and $A_3$ is $CR_2$ and the other is $CR_3$; and $R_1$, $R_2$ and $R_3$ are independently selected from hydrogen, halogen, CN, $OR_4$, $SR_4$, $N(R_4)_2$, $NHCOR_4$, $NHCOOCH_3$, $NHCOOC_2H_5$, $NHOR_4$, $NHNH_2$, $NO_2$, $COR_4$, $COR_5$, cyclopropyl, $C_{2-5}$ straight chain alkenyl, $C_{2-5}$ straight chain alkynyl or $C_{1-5}$ straight chain alkyl optionally terminally substituted with $OR_4$, $N(R_4)_2$, $SR_4$, $CO_2R_4$, $CON(R_4)_2$ or one, two or three halogen atoms, in which each $R_4$ is independently hydrogen or $C_{1-3}$ alkyl and $R_5$ is $OR_4$, $NH_2$ or $NHR_4$; or in which Z is a group $-C(R_7)=NR_6$ in which $R_6$ is a group $OR_8$, where $R_8$ is $C_{1-4}$ alkyl, $C_{2-4}$ alkenyl, $C_{2-4}$ alkynyl, a group $OCOR_9$ where $R_9$ is hydrogen or $R_8$, or a group $NHR_{10}$ or $NR_{11}R_{12}$ where $R_{10}$, $R_{11}$ and $R_{12}$ are independently $C_{1-2}$ alkyl and $R_7$ is hydrogen or $C_{1-4}$ alkyl, subject to the proviso that when $R_6$ is a group $OCOR_9$ or $NHR_{10}$, $R_7$ is $C_{1-4}$ alkyl.

The term halogen includes bromine, chlorine and fluorine.

Compounds of formula (I) in which Z is $-C(R_7)=NR_6$ are capable of existing as geometric isomers. The invention extends to each of these stereoisomeric forms, and to mixtures thereof. The different stereoisomeric forms may be separated one from the other by the usual methods, or any given isomer may be obtained by stereospecific synthesis.

The compounds of formula (I) can form acid addition salts with acids, such as the conventional pharmaceutically acceptable acids, for example hydrochloric, hydrobromic, phosphoric, acetic, fumaric, salicylic, citric, lactic, mandelic, tartaric, oxalic and methanesulphonic.

5-Membered aromatic heterocycles within the definition of variable Z include oxadiazole such as 1,2,4-oxadiazol-5-yl, 1,2,4-oxadiazol-3-yl and 1,3,4-oxadiazol-2-yl, oxazole such as 1,3-oxazol-2-yl, 1,3-oxazol-4-yl 1,3-oxazol-5-yl, 1,2-oxazol-3-yl and 1,2-oxazol-5-yl, thiadiazole such as 1,2,4-thiadiazol-5-yl and 1,3,4-thiadiazol-2-yl, thiazole such as 1,3-thiazol-2-yl, 1,3-thiazol-5-yl and 1,2-thiazol-5-yl, furan such as furan-2-yl and furan-3-yl, triazole such as 1-alkyl-, 2-alkyl- or 3-alkyl- 1,2,3-triazol-4-yl and 1,2,4-triazol-3-yl including 1-alkyl-1,2,4-triazol-3-yl, 1-alkyl-tetrazol-5-yl and 2-alkyl-tetrazol-5-yl, where 'alkyl' signifies a $C_{1-2}$ alkyl, cyclopropyl or propargyl group.

In a preferred aspect, variables $R_1$, $R_2$ and $R_3$ are independently selected from hydrogen, halogen, $N(R_4^1)_2$ in which each $R_4^1$ is independently hydrogen or methyl, straight chain $C_{2-3}$ alkenyl, straight chain $C_{2-3}$ alkynyl, cyclopropyl or straight chain $C_{1-5}$ alkyl optionally terminally substituted with $OR_4^2$ or one, two or three fluorine atoms, in which $R_4^2$ is methyl.

Values for $R_1$, $R_2$ and $R_3$ include hydrogen, methyl, methoxymethyl, ethyl, n-propyl, n-butyl, n-pentyl, cyclopropyl, but-2-enyl, $NH_2$ and $CH_2F$, preferably hydrogen, methyl, ethyl, n-propyl, n-butyl and n-pentyl.

It will be appreciated that the range of values for $R_1$, $R_2$ and $R_3$ will be limited by the preparative constraints and/or stability of the group Z. For example, an oxazole ring will tolerate a 2-amino substituent whereas 2-amino-furans are unstable. Conversely, 2-halo-furans are stable whereas 2-halo-oxazoles are very labile compounds. Where Z is a tri- or tetrazole group, the amino nitrogen must be substituted, preferably γ to the position of the azabicyclic moiety.

Examples of heterocyclic Z include 3-amino-1,2,4-oxadiazol-5-yl, 3-methyl-1,2,4-oxadiazol-5-yl, 1,3-oxazol-5-yl, 1,3-oxazol-2-yl, 3-ethyl-1,2,4-oxadiazol-5-yl, 3-propyl-1,2,4-oxadiazol-5-yl, 3-cyclopropyl-1,2,4-oxadiazol-5-yl, 3-butyl-1,2,4-oxadiazol-5-yl, 3-methoxymethyl-1,2,4-oxadiazol-5-yl, 3-pentyl-1,2,4-oxadiazol-5-yl, 3-but-2-enyl-1,2,4-oxadiazol-5-yl, fur-2-yl and 2-methyl-1,3,4-oxadiazol-5-yl.

The groups $R_8$ and $R_9$ in $R_6$ are preferably selected from methyl, ethyl, allyl and propargyl. $R_{10}$, $R_{11}$ and $R_{12}$ are preferably methyl. Suitable examples of $R_6$ include methoxy, ethoxy, allyloxy, propargyloxy, acetoxy and dimethylamino.

When $R_6$ is a group $OR_8$ or $NR_{11}R_{12}$, $R_7$ is preferably hydrogen or methyl.

When $R_6$ is a group $OCOR_9$ or $NHR_{10}$, $R_7$ is preferably methyl.

The invention also provides a process for the preparation of a compound of formula (I), or a pharmaceutically acceptable salt thereof, which process comprises cyclising a compound of formula (II):

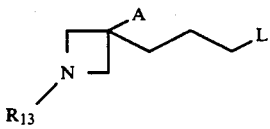

in which A represents Z or an electron withdrawing group convertible thereto, L is a leaving group and $R_{13}$ represents hydrogen or an N-protecting group, and thereafter, optionally or as necessary, removing any $R_{13}$ protecting group, converting A to Z, interconverting Z and/or forming a pharmaceutically acceptable salt.

Examples of the N-protecting group $R_{13}$ include benzyl and substituted benzyl. However, it is greatly preferred that $R_{13}$ is hydrogen.

Examples of the leaving group L include halo such as chloro.

Examples of A include $C_{1-4}$ alkoxycarbonyl and cyano, most preferably $C_{1-4}$ alkoxycarbonyl.

The cyclisation is preferably effected in a suitable solvent such as isopropanol under basic conditions at elevated temperature.

Conversion of A to a group Z, as defined for formula (I), may be carried out using procedures as described in, for example standard text books on heterocyclic chemistry such as 'Comprehensive Heterocyclic Chemistry', A. R. Katritzky and C. W. Rees, Pergamon, 1984.

The A group is first converted, as necessary, to a suitable starting group Z' for the chosen conversion reaction to give the required group Z.

A Z' carboxy group may be obtained by conventional de-esterification of an A alkoxycarbonyl group.

A Z' chlorocarbonyl group may be obtained by treatment of a Z' carboxy group by conventional routes under appropriate conditions.

A ' aminocarbonyl group may be obtained by treatment of a Z' chlorocarbonyl or, more preferably, an alkoxycarbonyl group with ammonia.

A Z' cyano group may be obtained by treatment of a Z' aminocarbonyl group with a dehydrating agent such as phosphorus pentoxide in toluene or trifluoroacetic acid anhydride in tetrahydrofuran and pyridine.

A Z' alkylcarbonyl group may be obtained from an A cyano group by treatment with the appropriate alkyl lithium in ether at depressed temperature, or by treatment of a LiOOC group with the appropriate alkyl lithium, the LiOOC group being obtained by hydrolysis of an A alkoxycarbonyl group with lithium hydroxide in water. Alternatively and less preferably, a Z' alkylcarbonyl group may be obtained by reaction of a Z' chlorocarbonyl group with N,O-dimethylhydroxylamine and treatment with an alkyl lithium or Grignard reagent.

A Z' bromomethylcarbonyl group may be obtained by treatment of a Z' COCH₃ group either with bromine in a suitable solvent such as methanol, the nitrogen of the azabicycle being protected as the hydrochloride or hydrobromide salt, or with lithium diisopropylamide and trimethylsilyl chloride at low temperature followed by N-bromosuccinimide in tetrahydrofuran at low temperature. Alternatively and less preferably, a Z' —COCl group may be converted to a —COCH₂Br group by treatment with diazomethane in ether at low temperature followed by hydrogen bromide in acetic acid at ambient temperature.

A Z' formyl group may be obtained by conventional reduction of an A alkoxycarbonyl group with a reducing agent such as diisobutylaluminium hydride in an inert solvent such as toluene at low temperature, or, alternatively and less preferably, hydrolysis with acid, followed by conversion to the acid chloride and reaction with O-N-methylated dimethyl hydroxylamine hydrochloride in the presence of pyridine in a suitable solvent such as dichloromethane to give the O-N-dimethyl amide. Reduction with diisobutyl aluminium hydride under similar conditions as above yields the required formyl group.

A Z' $CH_2N^+ \equiv C^-$ group may be obtained from a formamidomethyl group by treatment with phosgene and triethylamine. The formamidomethyl group may in turn be obtained from the aminomethyl group by reaction with an ester of formic acid such as ethyl formate. The aminomethyl group may be obtained by reduction of the aminocarbonyl group with lithium aluminium hydride.

When Z represents a 1,2,3-triazol-4-yl group, a Z' formyl group may be treated with triphenyl phosphine, carbon tetrabromide and zinc in an inert solvent such as dichloromethane at ambient temperature to provide a 2,2-dibromoethenyl group which may be eliminated with n-butyl lithium in hexane to give an ethynyl group. Treatment of the latter with azidotrimethyl silane in an inert solvent such as tetrahydrofuran at elevated temperature followed by lower alcohol at ambient temperature yields the unsubstituted 1,2,3-triazol-4-yl group which is alkylated as required. A 2-alkyl group may be introduced by treatment with the corresponding diazoalkane in ether at ambient temperature.

Alternatively a Z' acetyl group may be successively treated with hydrogen chloride, chlorine and triphenylphosphine to yield a triphenylphosphinemethylenecarbonyl group which may be treated with m-nitrobenzoyl azide in acetonitrile at elevated temperature to yield the 1,2,3-triazol-4-yl group which is protected at the 1 position by m-nitrobenzoyl. The protecting group may be removed by prolonged heating in a lower alcohol, by treatment with ammonia or by chromatography on basic alumina in a lower alcohol. The resulting unsubstituted 1,2,3-triazol-4-yl group may then be alkylated as described above.

Compounds of formula (I) in which Z represents a 1-alkyl or 3-alkyl-1,2,3-triazol-4-yl group may be obtained as minor products in the preparation of the corresponding 2-alkyl-1,2,3-triazol-4-yl compounds and chromatographically.

When Z represents a 2-alkyltetrazol-5-yl group, a Z' cyano group may be treated with azidotrimethyl silane in an inert solvent such as tetrahydrofuran at elevated temperature to yield a 2-trimethylsilyl-2H-tetrazol-5-yl group. Treatment of the latter with methanol effects deprotection of the amino nitrogen which may then be alkylated as described above.

Compounds of formula (I) in which Z represents a 1-alkyltetrazol-5-yl group may be obtained as a minor product in the preparation of the corresponding 2-alkyltetrazol-5-yl compound and separated chromatographically.

When Z represents a 1,2,4-triazol-3-yl group a Z' cyano group may be treated with dry ethanol saturated with hydrogen chloride gas to give an imidate. This may be treated with an alkyl hydrazine to form the corresponding amidrazone. Treatment of this with anhydrous formic acid or triethyl orthoformate will give the required 1-alkyl-1,2,4-triazol-3-yl group.

When Z represents 3-substituted-1,2,4-oxadiazol-5-yl, an alkoxycarbonyl group may be reacted with an appropriate amide oxime at elevated temperature in the presence of sodium alkoxide in a lower alcohol such as ethanol. The amide oxime is commercially available or may be prepared conventionally. For example, alkyl substituted amide oximes may be obtained by reacting hydroxylamine hydrochloride with the appropriate nitrile.

Alternatively, when Z represents 3-methyl-1,2,4-oxadiazol-5-yl, reaction of a Z' aminocarbonyl group with an acetal of N,N-dimethylacetamide such as the dimethyl or diethyl acetal at elevated temperature yields an acyl amidine group —CON=C(CH$_3$)N(CH$_3$)$_2$ which may then be reacted with hydroxylamine, in the presence of acid, such as acetic acid, which may also function as the solvent. The reaction may be carried out at ambient temperature, the N-hydroxy acyl amidine intermediate optionally isolated and then cyclised at elevated temperature, or alternatively in a single step at elevated temperature.

Alternatively and less preferably, a Z' chlorocarbonyl group may be reacted with an appropriate amide oxime, at elevated temperature in an inert, polar solvent such as chloroform, and the resulting substitution product cyclised at elevated temperature in a suitable solvent such as toluene or xylene.

When Z represents 3-amino-1,2,4-oxadiazol-5-yl, a Z' chlorocarbonyl or, more preferably, a carboxy ester group A may be reacted with a hydroxy guanidine derivative under basic conditions.

When Z represents optionally 3-substituted-1,2,4-thiadiazol-5-yl, a Z' aminocarbonyl group may be converted into an aminothiocarbonyl group using phosphorus pentasulphide or Lawesson's reagent (S. Scheibye, B. S. Pederson and J. O. Lawesson, Bull. Soc. Chim. Belg., 1978, 87 (3), 229). The aminothiocarbonyl may be converted into a thioacyl amidine group and cyclised as described above for the 1,2,4-oxadiazole group.

When Z represents 5-substituted-1,2,4-oxadiazol-3-yl, a Z' cyano group may be reacted with hydroxylamine, in a polar solvent such as methanol, to yield the corresponding amide oxime. The amide oxime may be cyclised using a suitable derivative of a carboxylic acid such as the anhydride or a trialkylorthoester such as triethyl orthoacetate, the acid derivative acting as the solvent, at elevated temperature.

When Z represents optionally 5-substituted-1,3,4-oxadiazol-2-yl, a Z' carboxy or carboxy ester group A may be converted to the acid hydrazide by conventional procedures. For example, the acid may be converted to a C$_{1-6}$ alkyl ester e.g. methyl, with the appropriate C$_{1-6}$ alkanol e.g. methanol under conventional esterification conditions, and the resulting ester reacted with hydrazine at ambient or elevated temperature to give the acid hydrazide. The acid hydrazide may then be cyclised by condensation with a suitable derivative of the appropriate carboxylic acid RCO$_2$H, e.g. an acyl halide or a trialkyl ortho-ester, such as the triethyl ortho-ester, the acid derivative acting as the solvent, at elevated temperature. Alternatively and preferably, the Z' carboxy ester group A may be converted to a diacyl hydrazide group —CONHNHCOR by treatment with the appropriate acyl hydrazide at ambient or elevated temperature. The diacyl hydrazide may then be cyclised by treatment with phosphorus pentoxide and methanesulphonic acid.

When Z represents optionally 5-substituted-1,3,4-thiaciazol-2-yl a Z' diacyl hydrazide group, —CONHNHCOR, obtained as described above can be cyclised using phosphorus pentasulphide. The cyclisation is preferably carried out in the absence of solvent with the nitrogen of the azabicycle protected as the hydrochloride salt.

When Z represents 1,3-oxazol-2-yl, the conversion may be effected by reaction of a Z' aminocarbonyl group with vinylene carbonate at elevated temperature in the presence of a strong acid such as polyphosphoric acid, which may also function as the solvent.

When Z represents optionally 5-substituted-1,3-oxazol-2-yl, a Z' carboxy group may first be converted to the carboxylic acid chloride and then reacted with a compound of formula NH$_2$CH$_2$CR(OR')$_2$, or more preferably the Z' carboxy group may be reacted directly with the compound of formula NH$_2$CH$_2$CR(OR')$_2$ in the presence of a condensing agent such as dicyclohexylcarbodiimide or a chloroformate ester such as ethyl chloroformate, to give a group CONHCH$_2$C(OR')$_2$R; which may be cyclised using a suitable dehydrating agent such as polyphosphoric acid, phosphorus oxychloride, phosphorus pentachloride, sulphuric acid or sulphuryl chloride, preferably polyphosphoric acid.

A Z optionally 5-substituted-1,3-thiazol-2-yl group may be obtained by cyclisation of a Z' —CONHCH$_2$C(OR')$_2$R group using phosphorus pentasulphide. The reaction is preferably carried out in the absence of solvent with the nitrogen of the azabicycle protected as the hydrochloride salt.

1,3-Oxazol-2-yl groups 4-methyl-substituted may be provided by the cyclisation of a Z' aminocarbonyl group with propargyl alcohol or acetate ester thereof, in the presence of a dehydrating agent such as polyphosphoric acid, using a catalyst such as HgSO$_4$, at elevated temperature.

Alternative routes to optionally 4-substituted 1,3-oxazol-2-yl groups include:

i) the condensation of a Z' aminocarbonyl group with the appropriate compound BrCH$_2$COR at elevated temperature; or ii) the reaction of a Z' carboxy group under basic conditions with the appropriate compound BrCH$_2$COR to give a group —COOCH$_2$COR which may be cyclised with ammonium chloride.

Where R is hydrogen the aldehyde is preferably protected as an acetal.

During the reaction (i) above, the nitrogen atom of the azabicyclic moiety may require protection.

When Z is optionally 4-substituted-1,3-thiazol-2-yl a Z' aminothiocarbonyl group may be reacted with the appropriate α-halo acyl compound such as BrCH$_2$COCH$_3$ as indicated for the corresponding 1,3-oxazole.

1,3-Oxazol-4-yl groups optionally 2-substituted may be provided by reacting a bromomethylcarbonyl group with an appropriate amide. Preferably, the reaction with acetamide is carried out at elevated temperature and the reaction with formamide is carried out in sulphuric acid.

An unsubstituted 1,3-oxazol-4-yl group may alternatively be obtained by treatment of a Z' —CH$_2$N$^+$≡C− group with a formate ester such as methyl formate after deprotonation with a strong base such as n-butyl lithium or potassium t-butoxide.

When Z represents optionally 3-substituted-1,2-oxazol-5-yl, the reaction of a Z' CH₃CO group may be carried out at depressed temperature with the appropriate ethyl ester in a suitable solvent such as toluene, under basic conditions such as sodium hydride and catalytic ethanol, followed by reflux, to yield the sodium salt of the resulting dicarbonyl compound. Cyclisation at ambient temperature with an aminating agent such as hydroxylamine-O-sulphonic acid in a dry solvent such as methanol, ethanol or diglyme, preferably in the presence of an acid such as sulphuric acid, p-toluene sulphonic acid or potassium hydrogen sulphate to minimise amination of the azabicycle, yields a compound of formula (I).

Alternatively, the dicarbonyl compound sodium salt may be treated prior to the cyclisation step with dimethylamine in ethanol in the presence of glacial acetic acid at ambient temperature to give the vinylogous amide which may be cyclised as described above.

When Z represents an optionally 5-substituted 1,2-oxazol-3-yl group, a Z' —C≡N⁺—O⁻ nitrile oxide group may be reacted with an olefin of the structure R—C(W)=CH₂, where W is halo such as chloro, OCOCH₃ or OSi(CH₃)₃. The highly reactive nitrile oxide may conveniently be generated in situ from an appropriate Z' halo oxime —C(Br)=NOH by treatment with a base such as triethylamine in a solvent such as N,N-dimethylformamide. The halo oxime is prepared by treatment of a Z' —CH=NOH oxime group with N-bromosuccinimide in N,N-dimethylformamide at ambient temperature, the azabicyclic being in the form of the hydrochloride salt. The Z' —CH=NOH oxime group may be prepared from a Z' —CHO group by reaction with hydroxylamine hydrochloride in a solvent such as methanol.

When Z represents an optionally 2-substituted-1,3-oxazol-5-yl group, a Z' —COCH₂Br group may be converted to —COCH₂NH₂ by treatment with NaN₃ in acetone or N,N-dimethylformamide followed by hydrogenation over a Pd/C catalyst in ethanolic HCl, or by treatment with hexamethylene tetramine followed by hydrolysis in methanolic HCl.

The —COCH₂NH₂ group may then be acylated with the appropriate derivative of formic acid such as acetic-formic anhydride or higher carboxylic acid such as the anhydride or chloride to yield an acyl amino ketone which can be cyclised using a suitable dehydrating agent such as polyphosphoric acid, sulphuric acid or phosphorous pentachloride at elevated temperature.

Alternatively, a Z' —CHO group may be treated with tosylmethyl isocyanide and anhydrous potassium carbonate in methanol under reflux followed by heating the 4-methoxyoxazoline product with polyphosphoric acid to afford a Z 1,3-oxazol-5-yl group.

When Z represents 2-furyl, a Z' CHO group may be treated with a reactive derivative of propanal such as the 3-tosyl derivative and in which the carbonyl group is preferably protected as a cyclic acetal (III):

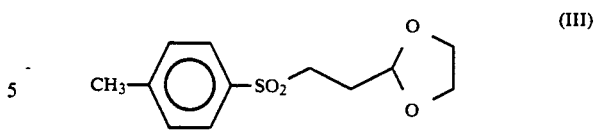

prepared by reaction of sodium 4-methylphenylsulphinate with 2-(2-bromoethyl)-1,3-dioxolane in dimethyl formamide at ambient temperature. The reaction of the compound of formula (III) with the Z' —CHO group in an inert solvent such as tetrahydrofuran in the presence of a base such as n-butyl lithium, initially at low temperature, rising to ambient, yields a compound of formula (IIIa):

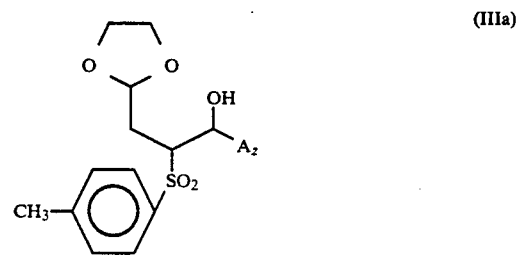

in which $A_z$ represents the azabicyclic moiety, which may be cyclised at elevated temperature in the presence of an acid such as glacial acetic acid which may also function as the solvent.

Alkyl-substituted 2-furyl groups may be obtained analogously using the appropriately substituted analogue of the compound of formula (III) prepared from the corresponding ketone or aldehyde.

A Z 1,3-thiazol-5-yl group may be obtained by dehydrating and cyclising the corresponding acyl amino ketone using phosphorous pentasulphide at elevated temperature.

Optionally 3-substituted 1,2-thiazol-5-yl groups may be prepared from the corresponding 1,2-oxazolyl group by ring opening effected by treatment with a reducing agent such as Raney nickel and hydrogen in a suitable solvent such as methanol or ethanol to yield a vinylogous amide which may be cyclised using phosphorous pentasulphide in the presence of a suitable oxidising agent such as sulphur or chloranil in a solvent such as toluene at elevated temperature.

Compounds of formula (I) in which Q contains a sulphur atom in place of oxygen may be prepared analogously. A sulphur-containing group Z' is obtained by treatment of a carbonyl-containing group Z' with either phosphorus pentasulphide or with Lawesson's reagent (S. Scheibye, B. S. Pederson and S. O. Lawesson, Bull. Soc. Chim. Belg., 1978, 87(3), 229). The resulting sulphur-containing group Z' may then be converted to the required sulphur-containing group Z analogously to the conversion of carbonyl-containing groups. Where the thiolating agent is phosphorus pentasulphide, this may also effect cyclisation.

In the above description, R represents H or alkyl as appropriate and R' represents $C_{1-6}$ alkyl such as methyl or ethyl or the R' groups together represent $C_{2-6}$ polymethylene such as ethylene.

Interconversion of carbon substituents $R_1$, $R_2$ and $R_3$ within a group Z may be carried out conventionally.

Thus an amino group may be converted to chloro, or —NHNH₂, via a diazonium intermediate.

Similarly a chloro substituent may be converted by reaction with a nucleophile such as methoxide; and alkoxycarbonyl groups may be converted, via carboxy, to an amino substituent.

When Z represents a —C(R₇)=NR₆ group, a Z' COR₇ group may be reacted with a compound of formula (IV).

  (IV)

wherein $R_6'$ represents $R_6$ or hydroxy, and thereafter converting $R_6'$ to $R_6$ when hydroxy.

The invention also provides a process for the preparation of a compound of formula (I) in which Z is —C(R₇)=NR₆, or a pharmaceutically acceptable salt thereof, which process comprises reacting a compound of formula (V):

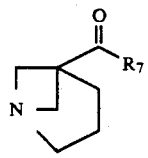  (V)

with a compound of formula (IV):

  (IV)

wherein $R_6'$ represents $R_6$ or hydroxy, converting $R_6'$ to $R_6$ when hydroxy, and thereafter forming a pharmaceutically acceptable salt.

The reaction between the compounds of formulae (V) and (IV) is preferably carried out in a hydroxylic solvent such as methanol or ethanol, at ambient temperature, or where appropriate, at elevated temperature.

Where $R_6$ in compounds of formula (I) is a group $OR_8$, $NHR_{10}$ or $NR_{11}R_{12}$, a compound of formula (V) is conveniently reacted with a compound of formula (IV) in which $R_6'$ is $R_6$.

Where $R_6$ in compounds of formula (I) is a group $OCOR_9$, a compound of formula (V) may be reacted with the compound of formula (IV) in which $R_6'$ is hydroxy, with subsequent acylation of the resulting oxime by treatment with a suitable acylating agent such as an acyl halide, for example acetyl chloride.

Novel intermediates of formula (VI) and salts thereof:

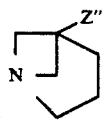  (VI)

wherein Z" is a group convertible to Z, also form part of the invention. A preferred value for Z" is an electron withdrawing group, most preferably $C_{1-4}$ alkoxycarbonyl. Compounds of formula (VI) may be prepared by the cyclisation of a compound of formula (II) in which $R_{13}$ is hydrogen and A is an electron withdrawing group, the conversion of the resulting Z" electron withdrawing group to other Z" and optionally forming a salt.

Compounds of formula (II) may be prepared by treatment of a compound of formula (VII):

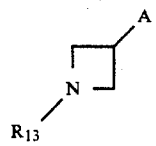  (VII)

wherein $R_{13}$ and A are as defined in formula (II), with a compound $L^1(CH_2)_3L$, wherein L is as defined in formula (II) and $L^1$ is a leaving group.

In compounds of formula (VII) it is preferred that $R_{13}$ is an N-protecting group and A is cyano. This can be converted to other A groups, such as $C_{1-4}$ alkoxycarbonyl by acid hydrolysis, before cyclisation of the compound of formula (II).

In the compound $L^1(CH_2)_3L$, the leaving group $L^1$ is preferably halo and preferably other than L, for example iodo.

The compound of formula (VII) in which $R_{13}$ is benzyl and A is cyano is described in EP-0169603.

Pharmaceutically acceptable salts of the compounds of formula (I) may be formed conventionally by reaction with the appropriate acid such as described above under formula (I).

The compounds of the present invention enhance acetylcholine function via an action at muscarinic receptors within the central nervous system and are therefore of potential use in the treatment and/or prophylaxis of dementia.

The present invention also provides a pharmaceutical composition, which comprises a compound of formula (I) or pharmaceutically acceptable salt thereof, and a pharmaceutically acceptable carrier.

The compositions may be in the form of tablets, capsules, powders, granules, lozenges, suppositories, reconstitutable powders, or liquid preparations such as oral or sterile parenteral solutions or suspensions.

In order to obtain consistency of administration it is preferred that a composition of the invention is in the form of a unit dose.

Unit dose presentation forms for oral administration may be tablets and capsules and may contain conventional excipients such as binding agents, for example syrup, acacia, gelatin, sorbitol, tragacanth, or polyvinyl pyrrolidone; fillers, for example lactose, sugar, maize-starch, calcium phosphate, sorbitol or glycine; tabletting lubricants, for example magnesium stearate; disintegrants, for example starch, polyvinylpyrrolidone, sodium starch glycollate or microcrystalline cellulose; or pharmaceutically acceptable wetting agents such as sodium lauryl sulphate.

The solid oral compositions may be prepared by conventional methods of blending, filling, tabletting or the like. Repeated blending operations may be used to distribute the active agent throughout those compositions employing large quantities of fillers. Such operations are of course conventional in the art. The tablets may be coated according to methods well known in normal pharmaceutical practice, in particular with an enteric coating.

Oral liquid preparations may be in the form of, for example, emulsions, syrups, or elixirs, or may be presented as a dry product for reconstitution with water or other suitable vehicle before use. Such liquid preparations may contain conventional additives such as suspending agents, for example sorbitol, syrup, methyl cellulose, gelatin, hydroxyethylcellulose, carboxymethylcellulose, aluminium stearate gel, hydrogenated edible fats; emulsifying agents, for example lecithin, sorbitan monooleate, or acacia; non-aqueous vehicles (which may include edible oils), for example almond oil, fractionated coconut oil, oily esters such as esters of glycerine, propylene glycol, or ethyl alcohol; preservatives, for example methyl or propyl p-hydroxybenzoate or sorbic acid; and if desired conventional flavouring or colouring agents.

For parenteral administration, fluid unit dosage forms are prepared utilizing the compound and sterile vehicle, and, depending on the concentration used, can be either suspended or dissolved in the vehicle. In preparing solutions the compound can be dissolved in water for injection and filter sterilized before filling into a suitable via or ampoule and sealing. Advantageously, adjuvants such as a local anaesthetic, a preservative and buffering agents can be dissolved in the vehicle. To enhance the stability, the composition can be frozen after filling into the vial and the water removed under vacuum. Parenteral suspensions are prepared in substantially the same manner, except that the compound is suspended in the vehicle instead of being dissolved, and sterilization cannot be sterilized by exposure to ethylene oxide before suspending in the sterile vehicle. Advantageously, a surfactant or wetting agent is included in the composition to facilitate uniform distribution of the compound.

The compositions may contain from 0.1% to 99% by weight, preferably from 10-60% by weight, of the active material, depending on the method of administration.

The invention also provides a method of treatment and/or prophylaxis of dementia in mammals including humans, which comprises administering to the sufferer an effective amount of a compound of formula (I) or a pharmaceutically acceptable salt thereof.

The dose of the compound used in the treatment of such disorders will vary in the usual way with the seriousness of the disorders, the weight of the sufferer, and the relative efficacy of the compound. However, as a general guide suitable unit doses may be 0.05 to 100 mg. for example 0.2 to 50 mg; and such unit doses may be administered more than once a day, for example two or three times a day, so that the total daily dosage is in the range of about 0.01 to 5 mg/kg; and such therapy may extend for a number of weeks or months.

Within the above indicated dosage ranges no toxicological effects are indicated for the compounds of the invention.

In a further aspect the invention provides a compound of formula (I) or a pharmaceutically acceptable salt thereof for use as an active therapeutic substance.

The invention further provides a compound of formula (I) or a pharmaceutically acceptable salt thereof, for use in the treatment and/or prophylaxis of dementia.

In another aspect the invention provides the use of a compound of formula (I) or a pharmaceutically acceptable salt thereof for the preparation of a medicament for the treatment and/or prophylaxis of dementia.

The following examples illustrate the invention and the following descriptions illustrate the preparation of intermediates thereto.

Description 1

1-Benzyl-3-(3-chloropropyl)azetidine-3-carbonitrile (D1)

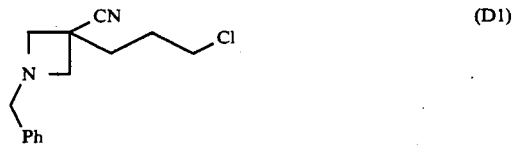

A stirred solution of lithium diisopropylamide (24 ml of 1.5M solution in cyclohexane, 0.036 mole) and N,N,N',N'-tetramethylethylenediamine (5.4 ml, 0.036 mole) in dry ether (300 ml) at −70° C. under nitrogen was treated dropwise over 5 minutes with a solution of 1-benzylazetidine-3-carbonitrile* (5.8 g, 0.034 mole) and 1-chloro-3-iodopropane (3.6 ml, 0.034 mole) in ether (40 ml). The resulting mixture was stirred at −65° C. for 15 minutes, then allowed to warm up to −40° C. over a further 15 minutes, before pouring into aqueous potassium carbonate solution (200 ml). The ether layer was separated and the aqueous further extracted with ethyl acetate (1×150 ml). The two organic solutions were combined, dried ($Na_2SO_4$) and concentrated in vacuo to leave an orange oil. This was purified by column chromatography on silica gel eluting initially with 10% ether/pentane to remove non-polar impurities and then with 50% ether/pentane to give the title compound (D1) as a colourless oil (5.35 g, 64%).

*see EP 0 169 603 A1

$^1$H Nmr (CDCl$_3$) δ: 1.86-2.02 (2H, m), 2.03-2.16 (2H, m), 3.25 (2H, d, J=8 Hz), 3.52 (2H, d, J=8 Hz), 3.60 (2H, t, 37 J=7 Hz), 3.65 (2H, s), 7.22-7.38 (5H, m)

Description 2

Methyl 1-benzyl-3-(3-chloropropyl)azetidine-3-carboxylate oxalate salt (D2)

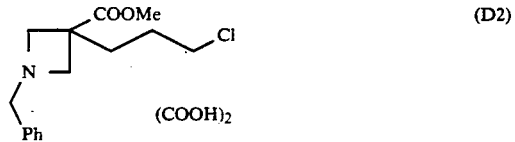

A stirred solution of 1-benzyl-3-(3-chloropropyl)azetidine-3-carbonitrile (D1, 5.35 g, 0.022 mole) in methanol (75 ml) was treated cautiously with concentrated sulphuric acid (15 ml) and then heated at 80° C. for 20 h. The solution was cooled in an ice bath and a further 12 ml of concentrated sulphuric acid added. The solution was heated at 80° C. for a further 9 hours, then allowed to cool, before pouring cautiously into ice/water (400 ml) with vigorous stirring. The aqueous mixture was basified by the addition of 0.88 ammonia solution, then extracted with ethyl acetate (2 ×200 ml). The combined extracts were dried ($Na_2SO_4$) and concentrated in vacuo to leave an orange oil, which was filtered through a basic alumina column eluting with ether. The colourless oil obtained was dissolved in ether (150 ml) and treated with a solution of oxalic acid (2.0 g, 0.022 mole) in methanol (10 ml). The title compound (D2) was filtered off as a white crystalline solid (7.25 g, 91%).

Free base: $^1$H NMR (CDCl$_3$) δ: 1.64–1.80 (2H, m), 2.00–2.13 (2H, m), 3.17 (2H, d, J=8 Hz), 3.49 (2H, d, J=8 Hz), 3.52 (2H, t, J=7 Hz), 3.62 (2H, s), 3.72 (3H, s), 7.20–7.35 (5H, m).

Description 3

Methyl 3-(3-chloropropyl) azetidine-3-carboxylate (D3)

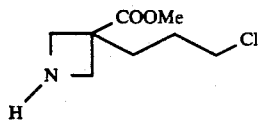

A solution of methyl 1-benzyl-3-(3-chloropropyl-)azetidine-3-carboxylate oxalate salt (D2, 6.73 g, 0.018 mole) in methanol (800 ml) was hydrogenated over 10% palladium on charcoal catalyst (1.4 g) at 40° C. and atmospheric pressure until the uptake of hydrogen ceased. The reaction mixture was filtered through a pad of kieselguhr and the filtrate concentrated in vacuo to give a white solid. This material was treated with excess concentrated potassium carbonate solution (50 ml) and extracted with chloroform (3×70 ml). The combined extracts were dried (Na$_2$SO$_4$) and concentrated in vacuo to give the title compound (D3) as a colourless oil (3.3 g, 96%).

$^1$H NMR (CDCl$_3$) δ: 1.63–1.78 (2H, m), 2.05–2.15 (2H, m), 2.25 (1H, br.s, NH), 3.42 (2H, d, J=8 Hz), 3.53 (2H, t, J=7 Hz), 3.73 (3H, s), 3.96 (2H, d, J=8 Hz).

Description 4

Methyl 1-azabicyclo3.1.1]hept-5-ylcarboxylate oxalate salt (D4)

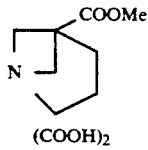

A solution of methyl 3-(3-chloropropyl)azetidine-3-carboxylate (D3, 3.3 g, 0.017 mole) in propan-2-ol (400 ml) was treated with anhydrous potassium carbonate (7.5 g, 0.054 mole) and heated under reflux for 18 h. The mixture was concentrated in vacuo and the residue treated with concentrated potassium carbonate solution (50 ml) and extracted with ethyl acetate (2×100 ml). The combined extracts were dried (Na$_2$SO$_4$) and concentrated in vacuo to leave a yellow oil (2.6 g), which was a 1:1 mixture of methyl and isopropyl esters. This was dissolved in methanol (200 ml), treated with a solution of sodium methoxide (0.045 mole) in methanol (40 ml) and stirred at room temperature for 2 h. The solution was cooled in ice, adjusted to pH 4 with methanolic hydrogen chloride and concentrated in vacuo. The residue was treated with excess concentrated potassium carbonate solution and extracted with ethyl acetate. The combined extracts were dried (Na$_2$SO$_4$) and concentrated in vacuo to leave a yellow oil, which was distilled in a Kugelröhr apparatus (b.p. approx. 100° C. at 0.2 mmHg) to give 600 mg (23%) of a colourless oil. A portion of this material was converted to its oxalate salt, which was recrystallised from methanol/ether to give the title compound (D4) as a white solid m.p. 114°–116° C.

Oxalate salt: $^1$H NMR (d$^6$ DMSO) δ: 2.08–2.20 (2H, m), 2.20–2.30 (2H, m), 3.35–3.45 (2H, m), 3.47–3.57 (2H, m), 3.65 (3H, s), 4.27–4.37 (2H, m).

$^{13}$C NMR (d$^6$DMSO) δ: 13.1, 26.6, 44.6, 48.2, 52.6, 57.5, 165.0, 170.5.

Analysis: C$_8$H$_{13}$NO$_2$·C$_2$H$_2$O$_4$. requires C: 48.98; H: 6.17; N: 5.71. found C: 49.22; H: 6.15; N: 5.84.

Description 5

Acetamide oxime (D5)

A solution of sodium methoxide, prepared from 2.90 g (0.126 mole) of sodium, in methanol (50 ml) was added to a stirred solution of hydroxylamine hydrochloride (8.7 g, 0.126 mole) in methanol (100 ml). The mixture was stirred at room temperature for 1 h, then filtered and the filtrate treated with acetonitrile (6.8 ml, 0.13 mole) and heated under reflux for 6 h. A further 6.8 ml of acetonitrile was added and reflux continued for a further 16 h. The solution was concentrated in vacuo to give the title compound (D5) as a white solid (7.7 g, 83%) m.p. 123°–127° C.

$^1$H NMR (d$^6$ DMSO) δ: 1.60 (3H, s), 5.35 (2H, br.s), 8.60 (1H, s)

Description 6

1-Azabicyclo[3.1.1]hept-5-ylcarboxaldehyde (D6)

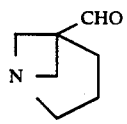

A stirred solution of methyl 1-azabicyclo[3.1.1]hept-5-ylcarboxylate (D4, 800 mg, 0.0052 mole) in dry toluene (15 ml) and hexane (15 ml) at −65° C. under nitrogen was treated with a 1.5M solution of diisobutylaluminium hydride in toluene (3.8 ml, 0.0056 mole). The reaction mixture was stirred at −65° C. for 0.75 h, then poured into excess 1M hydrochloric acid, with vigorous stirring. The mixture was basified with 10% sodium hydroxide solution, washed with ethyl acetate (1×60 ml) and the aqueous solution then saturated with potassium carbonate and extracted with chloroform (3×60 ml). The combined extracts were dried (Na$_2$SO$_4$) and concentrated in vacuo to give a colourless oil (620 mg), containing the title compound (D6). This was used without further purification.

Description 7

Propionamide oxime (D7)

A solution of hydroxylamine hydrochloride (6.90 g, 0.10 mole) in methanol (100 ml) was added to a stirred solution of sodium methoxide, prepared from 2.30 g (0.10 mole) of sodium in methanol (40 ml). The mixture was stirred at room temperature for 1 h, then filtered and the filtrate treated with propionitrile (7.9 ml, 0.11 mole) and heated under reflux for 12 h. The solution was concentrated in vacuo, the residue shaken with chloroform (200 ml) and then filtered through Kieselguhr. The filtrate was dried (Na$_2$SO$_4$) and concentrated in vacuo to give the title compound (D7) as a colourless oil (5.5 g, 62%).

$^1$H NMR (CDCl$_3$) δ: 1.12 (3H, t, J=7 Hz), 2.12 (2H, q, J=7 Hz), 4.60 (2H, br.s), 8.60 (1H, br.s).

IR (film) ν$_{C≡N}$ 1655cm$^{-1}$

Description 8

Butyramide oxime (D8)

The title compound (D8) was prepared from butyronitrile using the method given in Description 7, as a colourless oil (31%).

$^1$H NMR (CDCl$_3$+d$^6$DMSO) δ: 0.95 (3H, t, J=7 Hz), 1.60 (2H, sextet, J=7 Hz), 2.12 (2H, t, J=7 Hz), 4.75 (2H, br.s), 7.25 (1H, br.s).

Description 9

Cyclopropylcarboxamide oxime (D9)

The title compound (D9) was prepared from cyclopropylcarbonitrile using the method given in Description 7, as a pale green waxy solid (55%).

$^1$H NMR (CDCl$_3$+d$^6$DMSO) δ: 0.65–0.80 (4H, m), 1.40–1.53 (1H, m), 4.65 (2H, br.s), 8.20 (1H, br.s).

Description 10

Methoxyacetamide oxime (D10)

The title compound (D10) was prepared from methoxyacetonitrile using the method given in Description 7, as a pale pink solid (100%) m.p. 46°–49° C.

$^1$H NMR (CDCl$_3$) δ: 3.35 (3H, s), 3.94 (2H, s), 4.40 (2H, br.s), 5.00 (1H, br.s)

Description 11

Valeramide oxime (D11)

The title compound (D11) was prepared from valeronitrile using the method given in Description 7, as a pale green oil (53%).

$^1$H NMR (CDCl$_3$+d$^6$DMSO) δ: 0.92 (3H, t, J=7 Hz), 1.30–1.45 (2H, m), 1.50–1.70 (2H, m), 2.20 (2H, t, J=7 Hz), 5.40 (2H, br.s), 7.15 (1H, br.s)

Description 12

1-Azabicyclo[3.1.1]hept-5-ylcarboxamide (D12)

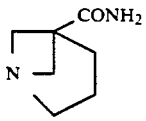

(D12)

Methyl 1-azabicyclo[3.1.1]hept-5-ylcarboxylate (D4, 1.35 g, 0.0087 mole) was treated with 20M aqueous ammonia solution (25 ml) and the mixture stirred at room temperature for 2 days. The solution was saturated with potassium carbonate and shaken with chloroform (40 ml) The mixture separated into three layers. The chloroform solution contained some product, however the majority was in the middle layer. These two were combined and concentrated in vacuo and the residue then treated with toluene (60 ml) and again concentrated in vacuo to azeotrope out the water. The title compound (D12) remained as a white solid (1.07 g, 88%) m.p. 188°–1920° C.

$^1$H NMR (d$^6$DMSO) δ: 1.80–1.93 (2H, m), 2.07–2.20 (2H, m), 2.60–2.68 (2H, m), 2.95 (2H, t, J=7 Hz), 3.35–3.45 (2H, m), 6.80 (1H, br.s), 7.05 (1H, br.s)

Description 13

Hexanoamide oxime (D13)

The title compound (D13) was prepared from hexanenitrile using the method given in Description 7, as a beige solid (73%) m.p. 40°–42° C.

$^1$H NMR (CDCl$_3$) δ: 0.90 (3H, t, J=7 Hz), 1.25–1.40 (4H, m), 1.50–1.65 (2H, m), 2.14 (2H, t, J=7 Hz), 4.55 (2H, br.s), 8.00 (1H, br.s).

Description 14

E-Pent-3-enamide oxime (D14)

The title compound (D14) was prepared from E-pent-3-enenitrile using the method given in Description 7, as a yellow oil (55%).

$^1$H NMR (CDCl$_3$+d$^6$ DMSO) δ: 1.60 (3H, d, J=7 Hz), 2.77 (2H, d, J=7 Hz), 4.80 (2H, br.s), 5.30–5.45 (1H, m), 5.48–5.65 (1H, m), 7.80 (1H, br.s).

Description 15

N'-Acetyl-1-azabicyclo[3.1.1]hept-5-ylhydrazide (D15)

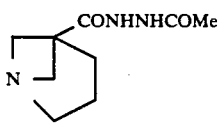

(D15)

A mixture of methyl 1-azabicyclo[3.1.1]hept-5-ylcarboxylate (D4, 770 mg, 0.0050 mole) and acethydrazide (410 mg, 0.0055 mole) in water (1.2 ml) was stirred at room temperature for 30 h, then warmed to 50° C. for a further 8 h. The solution was concentrated in vacuo, using toluene to azeotrope out the remaining traces of water. The title compound (D15) remained as a beige solid (980 mg, 100%).

$^1$H NMR (CD$_3$OD) δ: 1.95 (s, 3H), 2.25–2.45 (4H, m), 3.45–3.60 (4H, m), 4.28–4.37 (2H, m), 5.03 (2H, br.s).

Description 16

5-Acetyl-1-azabicyclo[3.1.1]heptane (D 16)

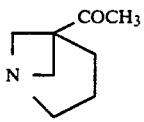

(D16)

A solution of methyl 1-azabicyclo[3.1.1]hept-5-ylcarboxylate (D4, 1.12 g, 0.0072 mole) in methanol (5 ml) was treated with a solution of lithium hydroxide monohydrate (308 mg, 0.0073 mole) in water (20 ml) and the resulting solution stirred at room temperature for 20 h, then concentrated in vacuo to leave a white solid which was dried thoroughly. A stirred suspension of this product in dry THF (120 ml) under nitrogen was treated at room temperature with 1M methyllithium in ether (8.0 ml, 0.0080 mole) and then heated under reflux for 3.5 h. The mixture was allowed to cool, then poured into excess well stirred cold 1M hydrochloric acid. The resulting solution was basified to saturation point with potassium carbonate and extracted with ethyl acetate (1×100 ml), followed by chloroform (2×60 ml). The combined extracts were dried (Na$_2$SO$_4$) and concentrated in vacuo to give the title compound (D 16) as a yellow oil (360 mg, 36%). This material was used without further purification.

$^1$H NMR (CDCl$_3$) δ: 1.95–2.08 (2H, m), 2.04 (3H, S), 2.16–2.30 (2H, m), 2.79–2.87 (2H, m), 3.17 (2H, t, J=7 Hz), 3.70–3.80 (2H, m)

EXAMPLE 1

5-(3-Amino-1,2,4-oxadiazol-5-yl)-1-azabicyclo[3.1.1]heptane (E1)

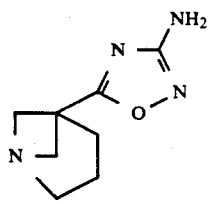

(E1)

A stirred solution of sodium ethoxide (0.019 mole) in ethanol (40 ml) at room temperature under nitrogen was treated with powdered 3A molecular sieves (4 g) and methyl 1-azabicyclo[3.1.1]hept-5-ylcarboxylate (D4, 370 mg, 0.0024 mole), followed by hydroxyguanidine hemisulphate hemi-hydrate (960 mg, 0.0072 mole). The mixture was heated under reflux for 1.25 h, then cooled in an ice bath and the pH adjusted to 5 by the addition of glacial acetic acid, before concentrating in vacuo. The residue was shaken with concentrated potassium carbonate solution (50 ml) and ethyl acetate (50 ml) then filtered through a plug of kieselguhr and the organic layer separated. The aqueous was extracted with chloroform (2×50 ml) and all three organic solutions combined, dried ($Na_2SO_4$) and concentrated in vacuo to leave a yellow gum. This was chromatographed on basic alumina eluting with 20% methanol/ethyl acetate to give the required material, which was triturated with ether to give the title compound (E1) as a white solid (32 mg, 7%) m.p. 167°–170° C.

$^1$H NMR (CDCl$_3$) δ: 2.00–2.20 (2H, m), 2.48 (2H, t, J=7 Hz), 2.98 (2H, dd, J=7 Hz and 2 Hz), 3.23 (2H, t, J=7 Hz), 4.01 (2H, dd, J=7 Hz and 2 Hz), 4.55 (2H, br.s, NH$_2$)

$^{13}$C NMR (CDCl$_3$) δ: 14.5, 29.3, 43.4, 52.7, 59 0, 167.9, 178.9

EXAMPLE 2

5-(3-Methyl-1,2,4-oxadiazol-5-yl)-1-azabicyclo[3.1.1]heptane oxalate salt (E2)

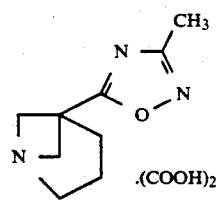

(E2)

To a stirred solution of sodium ethoxide, prepared from 390 mg (0.017 mole) of sodium in ethanol (30 ml) under nitrogen, was added powdered 3A molecular sieves (3 g), methyl 1-azabicyclo[3.1.1]hept-5-ylcarboxylate (D4, 430 mg, 0.0028 mole) and acetamide oxime (D5, 1.03 g, 0.014 mole). The mixture was heated under reflux for 1 h, then cooled in an ice bath and adjusted to pH 5 by the addition of glacial acetic acid. The mixture was concentrated in vacuo and the residue basified with concentrated potassium carbonate solution, then shaken well with ethyl acetate (100 ml) and filtered. The organic layer was separated, dried (Na$_2$SO$_4$) and concentrated in vacuo to leave an orange oil, which was chromatographed on basic alumina eluting initially with ether and then with 1:2 ether/ethyl acetate to give a pale yellow oil (290 mg). This was converted to its oxalate salt and recrystallised from ether/methanol to give the title compound (E2) as a white solid (270 mg, 36%) m.p. 153°–156° C.

Oxalate salt: $^1$H NMR (d$^6$DMSO) δ: 2.18–2.32 (2H, m), 2.35 (3H, s), 2.50 (2H, t, J=7 Hz), 3.51 (2H, t, J=7 Hz), 3.75 (2H, dd, J=7 Hz and 2 Hz), 4.52 (2H, dd, J=7 Hz and 2 Hz).

$^{13}$C NMR (d$^6$DMSO) δ: 11.04, 11.06, 13.18, 26.60, 47 92, 58.36, 164.68, 167.02, 176.43

Analysis: C$_9$H$_{13}$N$_3$O.C$_2$H$_2$O$_4$. requires C: 49.07; H: 5.62; N; 15.61%. found C: 48.97; H: 5.62; N: 15.55%.

EXAMPLE 3

5-(1,3-Oxazol-5-yl)-1-azabicyclo[3.1.1]heptane oxalate salt (E3)

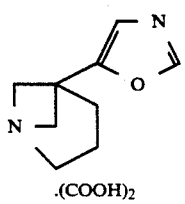

(E3)

A stirred solution of crude 1-azabicyclo[3.1.1]hept-5-ylcarboxaldehyde (D6, 620 mg, 0.0050 mole) in methanol (15 ml) was treated with anhydrous potassium carbonate (830 mg, 0.0060 mole) and tosylmethyl isocyanide (1.07 g, 0.0055 mole). The mixture was heated under reflux for 1.5 h, then concentrated in vacuo and the residue treated with concentrated potassium carbonate solution (10 ml) and extracted with chloroform (3×30 ml). The combined extracts were dried (Na$_2$SO$_4$) and concentrated in vacuo to leave a yellow oil, which was treated with polyphosphoric acid (20 g) and heated at 140° C. for 0.25 h. The hot solution was poured cautiously into excess cold potassium carbonate solution, with good stirring. The mixture was extracted with ethyl acetate (2×50 ml) and the combined extracts dried (Na$_2$SO$_4$) and concentrated in vacuo to leave an orange oil. This was chromatographed on basic alumina eluting with ethyl acetate. The colourless oil obtained was converted to its oxalate salt and crystallised from methanol/acetone to give the title compound (E3) as a pale yellow solid (12 mg) m.p. 139°–143° C.

Oxalate salt: $^1$H NMR (CD$_3$OD) δ: 2.32–2.47 (2H, m), 2.47–2.60 (2H, m), 3.63 (2H, t, J=7 Hz), 3.76 (2H, dd, J=7 Hz and 2 Hz), 4.58 (2H, dd, J=7 Hz and 2 Hz), 7.15 (1H, s), 8.24 (1H, s).

MS: C$_9$H$_{12}$N$_2$O requires M+ =164.0949, found M+ =164.0951.

EXAMPLE 4

5-(1,3-Oxazol-2-yl)-1-azabicyclo[3.1.1]heptane oxalate salt (E4)

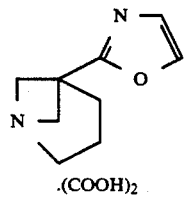

(E4)

A well stirred mixture of 1-azabicyclo[3.1.1]hept-5-ylcarboxamide (D12, 640 mg, 0.0046 mole) and vinylene carbonate (600 mg, 0.0069 mole) in polyphosphoric acid (25 g) was heated at 120° C. for 1 h. The hot solution was then poured cautiously, with good stirring, into excess potassium carbonate solution. The aqueous mixture was saturated with potassium carbonate and extracted with ethyl acetate (1×100 ml), followed by chloroform (1×100 ml). The combined extracts were dried ($Na_2SO_4$) and concentrated in vacuo at room temperature. The residue was immediately chromatographed on basic alumina eluting initially with ethyl acetate, increasing to 15% methanol/ethyl acetate to give a colourless oil (60 mg). This was converted to its oxalate salt and recrystallised from methanol/ether to give the title compound (E4) as a white solid (65 mg, 6%) m.p. 165°–166° C.

$^1$H NMR (d$^6$DMSO) δ: 2.20–2 33 (2H, m), 2.45–2.55 (2H, m), 3.52 (2H, t, J=7 Hz), 3.75 (2H, dd, J=7 Hz and 2 Hz), 4.47 (2H, dd, J=7 Hz and 2 Hz), 7.27 (1H, s), 8.18 (1H, s).

Analysis: $C_9H_{12}N_2O.C_2H_2O_4$. requires C: 51.97; H: 5.55; N: 11.02%. found C: 51.74; H: 5.55; H: 10.73%.

EXAMPLE 5

5-(3-Ethyl-1,2,4-oxadiazol-5-yl)-1-azabicyclo[3.1.1]heptane oxalate salt (E5)

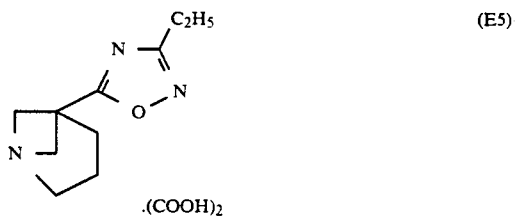

(E5)

The title compound (E5) was prepared from methyl 1-azabicyclo[3.1.1]hept-5-ylcarboxylate (D4) and propionamide oxime (D7) using the method given in Example 2, as a white Solid (39%) m.p. 148°–150° C.

Oxalate salt: $^1$H NMR (d$^6$DMSO) δ: 1.24 (3H, t, J=7 Hz), 2.17–2.32 (2H, m), 2.45–2.52 (2H, m), 2.74 (2H, q, J=7 Hz), 3.50 (2H, t, J=7 Hz), 3.77 (2H, dd, J=7 Hz and 2 Hz), 4.50 (2H, dd, J=7 Hz and 2 Hz).

Analysis: $C_{10}H_{15}N_3O.C_2H_2O_4$. requires C: 50.88; H: 6.05; N: 14.83%. found C: 50.66; H: 6.00; N; 14.80%.

EXAMPLE 6

5-(3-Propyl-1,2,4-oxadiazol-5-yl)-1-azabicyclo[3.1.1]heptane oxalate salt (E6)

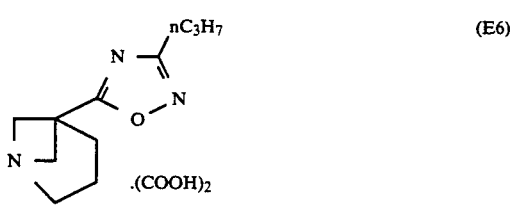

(E6)

The title compound (E6) was prepared from methyl 1-azabicyclo[3.1.1]hept-5-ylcarboxylate (D4) and butyramide oxime (D8) using the method given in Example 2, as a white solid (33%) m.p. 135°–137° C.

Oxalate salt: $^1$H NMR (d$^6$DMSO) δ: 0.93 (3H, t, J=7 Hz), 1.69 (2H, sextet, J=7 Hz), 2.17–2.32 (2H, m), 2.45–2.55 (2H, m), 2.68 (2H, t, J=7 Hz), 3.50 (2H, t, J=7 Hz), 3.76 (2H, dd, J=7 Hz and 2 Hz), 4.50 (2H, dd, J=7 Hz and 2 Hz).

Analysis: $C_{11}H_{17}N_3O.C_2H_2O_4$. requires C: 52.52; H: 6.44; N: 14.13%. found C:52.35; H: 6.44; N: 14.22%.

EXAMPLE 7

5-(3-Cyclopropyl-1,2,4-oxadiazol-5-yl)-1-azabiciclo[3.1.1]heptane oxalate salt (E7)

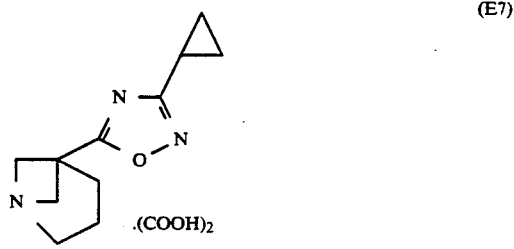

(E7)

The title compound (E7) was prepared from methyl 1-azabicyclo[3.1.1]hept-5-ylcarboxylate (D4) and cyclopropylcarboxamide oxime (D9) using the method given in Example 2, as a white solid (36%) m.p. 149°–150° C.

Oxalate salt: $^1$H NMR (d$^6$CMSO) 0.85–0.93 (2H, m), 1.02–1.14 (2H, m), 2.07–2.30 (3H, m), 2.40–2.53 (2H, m), 3.47 (2H, t, J=7 Hz), 3.72 (2H, dd, J=7 Hz and 2 Hz), 4.45 (2H, dd, J=7 Hz and 2 Hz)

Analysis: $C_{11}H_{15}N_3O.C_2H_2O_4$. requires C: 52.88; H: 5.80; N: 14.23%. found C: 52.75; H: 5.80; N: 14.06%.

EXAMPLE 8

5-(3-Butyl-1,2,4-oxadiazol-5-yl)-1-azabicyclo[3.1.1]heptane oxalate salt (E8)

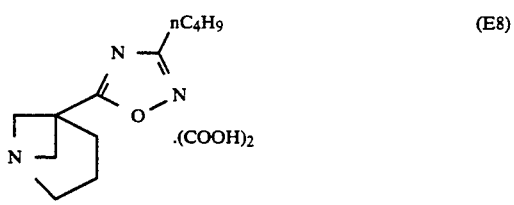

(E8)

The title compound (E8) was prepared from methyl 1-azabicyclo[3.1.1]hept-5-ylcarboxylate (D4) and valeramide oxime (D11) using the method given in Example 2, as a white solid (37%) m.p. 128°–130° C.

Oxalate salt: $^1$H NMR (d$^6$DMSO) δ: 0.88 (3H, t, J=7Hz), 1.25–1.40 (2H, m), 1.55–1.70 (2H, m), 2.15–2.30 (2H, m), 2.45–2.55 (2H, m), 2.68 (2H, t, J=7 Hz), 3.48 (2H, t, J=7 Hz), 3.74 (2H, dd, J=7 Hz and 2 Hz), 4.50 (2H, dd, J=7 Hz and 2 Hz).

Analysis: $C_{12}H_{19}N_3O.C_2H_2O_4$. requires C: 54.01; H: 6.80; N: 13.50%. found C: 53.88; H: 6.87; N: 13.28%.

EXAMPLE 9

5-(3-Methoxymethyl-1,2,4-oxadiazol-5-yl)-1-azabicyclo-[3.1.1]heptane oxalate salt (E9)

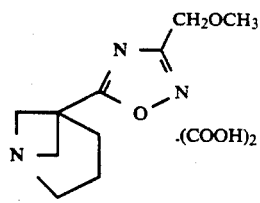

A stirred solution of sodium methoxide, prepared from 290 mg (0.012 mole) of sodium in methanol (20 ml), under nitrogen was treated with methyl 1-azabicyclo[3.1.1]hept-5-ylcarboxylate (D4, 300 mg, 0.0019 mole), methoxyacetamide oxime (D10, 1.0 g, 0.0097 mole) and powdered 3A molecular sieves (2.5 g). The mixture was heated under reflux for 3.5 h, then cooled in an ice bath and adjusted to pH 6 by the addition of glacial acetic acid. The mixture was concentrated in vacuo and the residue basified with concentrated potassium carbonate solution, then shaken with ethyl acetate (100 ml). The mixture was filtered and the organic layer separated, dried ($Na_2SO_4$) and concentrated in vacuo to leave a yellow oil. This material was chromatographed twice on basic alumina, each time eluting initially with ether then with 20% ethyl acetate/ether to eventually give a colourless oil (80 mg). This was converted to its oxalate salt and crystallised from acetone to give the title compound (E9) as a white solid (12%) m.p. 102°-104° C.

Oxalate salt: $^1$H NMR ($d^6$DMSO) δ: 2.15-2.30 (2H, m), 2.47-2.55 (2H, m), 3.33 (3H, s), 3.50 (2H, t, J=7 Hz), 3.77 (2H, dd, J=7 Hz and 2 Hz), 4.53 (2H, dd, J=7 Hz and 2 Hz), 4.55 (2H, s).

EXAMPLE 10

5-(3-Pentyl-1,2,4-oxadiazol-5-yl)-1-azabicyclo3.1.1]heptane oxalate salt (E10)

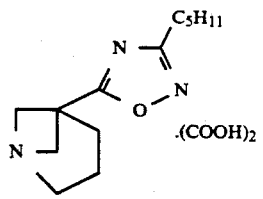

The title compound (E10) was prepared from methyl 1-azabicyclo[3.1.1]hept-5-yl-carboxylate (D4) and hexanoamide oxime (D13) using the method given in Example 2, as a white solid (32%) m.p. 127°-129° C.

Oxalate salt: $^1$H NMR ($d^6$DMSO) δ: 0.87 (3H, t, J=7 Hz), 1.25-1.40 (4H, m), 1.57-1.73 (2H, m), 2.15-2.30 (2H, m), 2.45-2.55 (2H, m), 2.68 (2H, t, J=7 Hz), 3.50 (2H, t, J=7 Hz), 3.75 (2H, dd, J=7 Hz and 2 Hz), 4.50 (2H, dd, J=7 Hz and 2 Hz).

Analysis: $C_{13}H_{21}N_3O.C_2H_2O_4$. requires C: 55.37; H: 7 13; N: 12.92%. found C: 55.53; H: 7.16; N: 12.91%.

EXAMPLE 11

E-5-(3-But-2-enyl-1,2,4-oxadiazol-5-yl)-1-azabicyclo[3.1.1]heptane oxalate salt (E11)

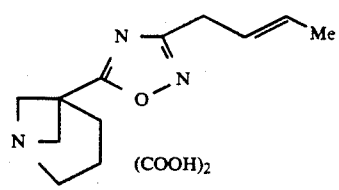

Methyl 1-azabicyclo[3.1.1]hept-5-ylcarboxylate (D4) was treated with E-pent-3-enamide oxime (D14) using the procedure described for Example 2. The crude product was purified by chromatography on basic alumina eluting initially with 1:1 ether/pentane and then with neat ether to give a colourless oil. This was converted to its oxalate salt and recrystallised from methanol/ether to give a white solid (25%) containing 90% of the title compound (E11) and 10% of the corresponding 1-butene isomer. m.p. 132°-135° C.

Oxalate salt:
$^1$H NMR ($d^6$ DMSO) δ: (major isomer) 1.64 (3H, d, J=7 Hz), 2.16-2.32 (2H, m), 2.43-2.57 (2H, m), 3.40-3.57 (4H, m), 3.75 (2H, dd, J=7 Hz and 2 Hz), 4.48 (2H, dd, J=7 Hz and 2 Hz), 5.48-5.74 (2H, m).

$^{13}$C NMR ($d^6$ DMSO) δ: (major isomer) 13.22, 17.66, 26.66, 28.64, 38.96, 47.96, 58.41, 124.30, 128.76, 164.78 $(COOH)_2$, 169.16, 176.65.

EXAMPLE 12

5-(Fur-2-yl)-1-azabicyclo3.1.1]heptane (E12)

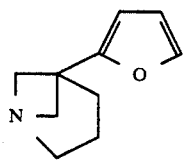

A stirred solution of lithium diisopropylamide (4.0 ml of 1.5M cyclohexane solution; 0.0060 mole) in dry tetrahydrofuran (100 ml) at −65° C. under nitrogen was treated with a solution of 2-[2-(4-methylphenylsulphonyl)ethyl]-1,3-dioxolane (compound D5 in EP-0322182, 1.54 g, 0.0060 mole) in dry tetrahydrofuran (5 ml). After stirring the resulting solution at −65° C. for 10 minutes, a solution of crude 1-azabicyclo[3.1.1]hept-5-ylcarboxaldehyde (D6, 550 mg, 0.0044 mole) in dry THF (8 ml) was added. The reaction mixture was allowed to warm up to −20° C. over 30 minutes, then treated with glacial acetic acid (5 ml) and concentrated in vacuo. The residue was dissolved in glacial acetic acid (100 ml), treated with 4-toluenesulphonic acid (20 mg) and heated under reflux for 24 h. The solution was concentrated in vacuo and the residue basified with concentrated potassium carbonate solution and extracted with chloroform (2×80 ml). The combined extracts were dried ($Na_2SO_4$) and concentrated in vacuo to leave a brown oil, which was distilled in a Kugelröhr apparatus. The material boiling at 130°-150° C. at 0.1 mmHg was collected and then chromatographed on basic alumina eluting initially with ether to remove impurities, then with 10% methanol/ethyl acetate to remove the title compound (E12), which was obtained as a colourless oil (4 mg).

$^1$H NMR (CDCl$_3$) δ: 1.93–2.08 (2H, m), 2.25–2.35 (2H, m), 2.84–2.94 (2H, m), 3.17 (2H, t, J=7 Hz), 3.86–3.95 (2H, m), 5.92–5.95 (1H, m), 6.20–6.25 (1H, m), 7.25–7.28 (1H, m).

EXAMPLE 13

5-(2-Methyl-1,3,4-oxadiazol-5-yl)-1-azabicyclo[3.1.1-]heptane oxalate salt (E13)

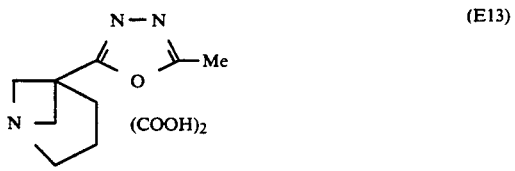

A mixture of phosphorus pentoxide (2.8 g, 0.025 mole) and methanesulphonic acid (28 g, 0.25 mole) was stirred at room temperature for 1 h, then added to N'-acetyl-1-azabicyclo[3.1.1]hept-5-ylhydrazide (D15, 980 mg, 0.0050 mole) and the mixture heated at 70° C. for 2 h. The solution was allowed to cool, then added carefully to excess cold concentrated potassium carbonate solution, with good stirring. The mixture was extracted with chloroform (2×70 ml) combined extracts dried (Na$_2$SO$_4$) and concentrated in vacuo to leave a yellow oil. This was chromatographed on basic alumina eluting with 10% methanol/ethyl acetate and the colourless oil obtained converted to its oxalate salt. This was recrystallised from methanol/ether to give the title compound (E13) as a white solid (190 mg, 14%) m.p. 149°–150° C. Oxalate:

$^1$H NMR (d$^6$ DMSO) δ: 2.18–2.32 (2H, m), 2.43–2.57 (2H, m), 2.48 (3H, s), 3.50 (2H, t, J=7 Hz), 3.76 (2H, dd, J=7 Hz and 2 Hz), 4.47 (2H, dd, J=7 Hz and 2 Hz).

Analysis: C$_9$H$_{13}$N$_3$O.C$_2$H$_2$O$_4$. requires C: 49.07; H: 5.62; N: 15.61%. found C: 48.93; H: 5.63; N: 15.83%.

EXAMPLE 14

E-1-Azabicyclo[3.1.1]hept-5-ylcarboxaldehyde-O-methyloxime oxalate salt (E14)

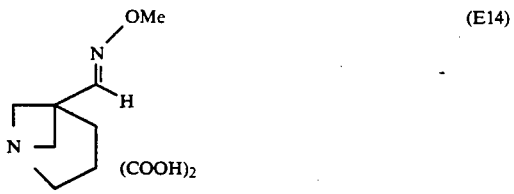

A solution of crude 1-azabicyclo[3.1.1]hept-5-ylcarboxaldehyde (D6, 0.0026 mole) in methanol (15 ml) was treated with 0-methylhydroxylamine hydrochloride (220 mg, 0.0026 mole) and the resulting solution left to stand for 2 days at room temperature. The solution was concentrated in vacuo, the residue basified with concentrated potassium carbonate solution and extracted with chloroform (2×50 ml). The combined extracts were dried (Na$_2$SO$_4$) and concentrated in vacuo to leave a pale yellow oil, which was chromatographed on basic alumina eluting with 10% methanol/ethyl acetate. The colourless oil obtained was converted to its oxalate salt and recrystallised from methanol/ether to give the title compound (E14) as a white solid (80 mg, 13%) m.p. 126°–129° C.

Oxalate salt: $^1$H NMR (d$^6$DMSO) δ: 2.05–2.20 (4H, m), 3.38–3.53 (4H, m), 3.75 (3H, s), 4.15–4.25 (2H, m), 7.47 (1H, s).

Analysis: C$_8$H$_{14}$N$_2$O.C$_2$H$_2$O$_4$. requires C: 49.18; H: 6.60; N: 11.47%. found C: 49.08; H: 6.65; N: 11.36%.

The hydrochloride salt is obtained analogously from the free base using hydrogen chloride in ether.

EXAMPLE 15

E and Z-5-Acetyl-1-azabicyclo[3.1.1]heptane O-methyloxime oxalate salt (E15)

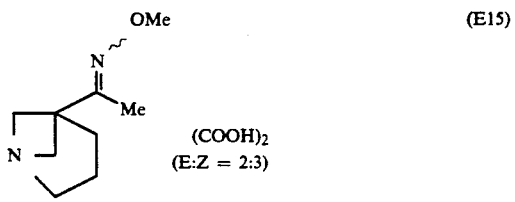

A stirred solution of 5-acetyl-1-azabicyclo[3.1.1]heptane (D16, 360 mg, 0.0026 mole) in methanol (20 ml) was treated with O-methylhydroxylamine hydrochloride (250 mg, 0.0030 mole) and left at room temperature for 20 h. The solution was concentrated in vacuo and the residue basified with concentrated potassium carbonate solution and extracted with chloroform (2×60 ml). The combined extracts were dried (Na$_2$SO$_4$) and concentrated in vacuo to leave a brown oil, which was chromatographed on basic alumina eluting with 5% methanol/ethyl acetate. The pale yellow oil obtained was converted to its oxalate salt and crystallised from methanol/ether to give the title compound (E15) as a 2:3 mixture of E:Z isomers, as a white solid (110 mg, 14%) m.p. 110°–116° C.

Oxalate salt: $^1$H NMR (2:3 mixture of E/Z isomers) (d$^6$DMSO) δ: 1.70 and 1.71 (together 3H, 2×s), 2.05–2.20 (4H, m), 3.35–3.45 (2H, m), 3.47–3.60 (2H, m), 3.67 (s, CH$_3$, Z-isomer), 3.76 (s, CH$_3$, E-isomer), 4.13–4.25 (2H, m)

Biological Activity

Radio ligand Binding

Cerebral cortex from Hooded Lister rats (Olac, UK) is homogenised in 2.5 vols ice-cold 50 mM tris buffer pH 7.7 (at 25° C.). After centrifugation at 25,000×g at 4° C. for 15 min the pellet is resuspended in 2.5 vols buffer and the wash repeated 3 times more. The final resuspension is in 2.5 volumes and the homogenates are stored in 1 ml aliquots at −20° C.

Incubations (total volume 2 ml) are prepared using the above buffer with the addition of 2 mM magnesium chloride in the 3H-Oxotremorine-M (3H-OXO-M) experiments. For 3H-Quinuclidinyl Benzilate (3H-QNB), 1 ml of stored membranes is diluted to 30 ml and 0.1 ml mixed with test compound and 0.27 nM (c. 25,000 cpm) 3H-QNB (Amersham International). For 3H-OXO-M, 1 ml of membranes is diluted to 6 ml and 0.1 ml mixed with test compound and 2 nM (c. 250,000 cpm) 3H-OXO-M (New England Nuclear).

Non-specific binding of 3H-QNB is defined using 1 μM Atropine sulphate (2 μM Atropine) and of 3H-OXO-M using 10 μM Oxotremorine. Non-specific binding values typically are 5% and 25% of total binding, respectively. Incubations are carried out at 37° C. for 30 min and the samples filtered using Whatman GF/B filters. (In the 3H-OXO-M experiments the filters are presoaked for 30 min in 0.05% polyethylenimine in water). Filters are washed with 3×4 ml ice-cold buffer. Radioactivity is assessed using a Packard BPLD scintillation counter, 3 ml Pico-Fluoro 30 (Packard) as scintillant.

This test provides an indication of the muscarinic binding activity oft he test compound. The results are obtained as $IC_{50}$ values (i.e. the concentration which inhibits binding of the ligand by 50%) for the displacement of the muscarinic agonist 3H-OXO-M and the muscarinic antagonist 3H-QNB. The ratio $IC_{50}$(3H-QNB)/$IC_{50}$(3H-OXO-M) gives an indication of the agonist character of the compound. Agonists typically exhibit a large ratio; antagonists typically exhibit a ratio near to unity.

The results are shown in Table 1.

TABLE 1

| Example | $^3$H-OXO-M $IC_{50}$ (nM) | $^3$H-QNB $IC_{50}$ (nM) |
|---|---|---|
| E1 | 11 | 11000 |
| E2 | 15 | 5000 |
| E3 | 37 | 6250 |
| E4 | 540 | 60000 |
| E5 | 71 | 5200 |
| E6 | 40 | 1700 |
| E7 | 62 | 580 |
| E8 | 49 | 1950 |
| E9 | 178 | 13000 |
| E10 | 141 | 2400 |
| E11 | 165 | 1850 |
| E13 | 207 | 16500 |
| E14 | 109 | 24000 |
| E15 | 290 | 58000 |

I claim:

1. A compound of formula (VI) or a salt thereof:

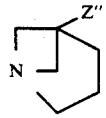 (VI)

wherein Z" is a group convertible to Z as defined in claim 12, and wherein Z" is selected from the group consisting of cyano, alkoxycarbonyl, carboxy, chlorocarbonyl, amino carbonyl, alkyl carbonyl, bromomethylcarbonyl, formyl, isocyanomethyl, formamido methyl, aminothiocabonyl, thioacylamidine, diacylhydrazide, nitrile oxide, halo oxime, aminomethyl carbonyl.

2. Methyl 1-azabicyclo[3.1.1]hept-5-ylcarboxylate, 1-azabicyclo[3.1.1]hept-5-ylcarboxaldehyde, 1-azabicyclo[3.1.1]hept-5-ylcarboxamide, N'-acetyl-1-azabicyclo 3.1.1.]hept-5-ylhydrazide or 5-acetyl-1-azabicyclo[3.1.1]heptane.

3. A process for the preparation of a compound of formula (I) or a pharmaceutically acceptable salt thereof comprising:

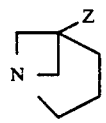 (I)

in which Z is a heterocyclic group

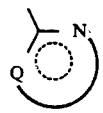

in which Q represents a 3-membered divalent residue completing a 5-membered aromatic ring and comprises one or two heteroatoms selected from oxygen, nitrogen and sulphur, or three nitrogen atoms, any amino nitrogen being substituted by a $C_{1-2}$ alkyl, cyclopropyl or propargyl group, and any ring carbon atom being optionally substituted by a group $R_1$; or a group

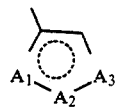

in which $A_1$, $A_2$ and $A_3$ complete a 5-membered aromatic ring and $A_1$ is oxygen or sulphur, one of $A_2$ and $A_3$ is $CR_2$ and the other is nitrogen or $CR_3$, or $A_2$ is oxygen or sulphur, one of $A_1$ and $A_3$ is $CR_2$ and the other is $CR_3$; and $R_1$, $R_2$, and $R_3$ are independently selected from hydrogen, halogen, CN, $OR_4$, $SR_4$, $N(R_4)_2$, $NHCOR_4$, $NHCOOCH_3$, $NHCOOC_2H_5$, $NHOR_4$, $NHNH_2$, $NO_2$, $COR_4$, $COR_5$, cyclopropyl, $C_{2-5}$ straight chain alkenyl, $C_{2-5}$ straight chain alkynyl or $C_{1-5}$ straight chain alkyl optionally terminally substituted with $OR_4$, $N(R_4)_2$, $SR_4$, $CO_2R_4$, $CON(R_4)_2$ or one, two or three halogen atoms, in which $R_4$ is independently hydrogen or $C_{1-3}$ alkyl and $R_5$ is $OR_4$, $NH_2$ or $NHR_4$; or in which Z is a group —C$_{(7)}$=NR$_6$ in which $R_6$ is a group $OR_8$, where $R_9$ is hydrogen or $R_8$, or a group $NHR_{10}$ or $NR_{11}R_{12}$ where $R_{10}$, $R_{11}$ and $R_{12}$ are independently $C_{1-2}$ alkyl and $R_7$ is hydrogen or $C_{1-4}$ alkyl, subject to the proviso that when $R_6$ is a group $OCOR_9$ or $NHR_{10}$, $R_7$ is $C_{1-4}$ alkyl, said process comprising cyclizing a compound of formula (II)

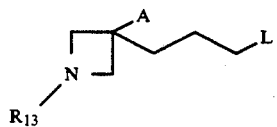 (II)

in which A represents Z or an electron withdrawing group convertible thereto, L is a leaving group and $R_{13}$ represents hydrogen or an N-protecting group, and thereafter, optionally or as necessary, removing any $R_{13}$ protecting group, converting A to Z, interconverting Z and/or forming a pharmaceutically acceptable salt.

* * * * *

UNITED STATES PATENT AND TRADEMARK OFFICE
CERTIFICATE OF CORRECTION

PATENT NO. : 5,157,160
DATED : October 20, 1992
INVENTOR(S) : Paul A. Wyman

It is certified that error appears in the above-indentified patent and that said Letters Patent is hereby corrected as shown below:

Col. 25, claim 2, line 4, change "3.1.1.]hept-5-ylhydrazide" to —[3.1.1]hept-5-ylhydrazide—.

Col. 26, claim 3, line 28 (counting each formula as one line), change "—C($_7$)=NR$_6$" to, — —C(R$_7$)=NR$_6$ —; and line 29, after "a group OR$_8$" insert —where R$_8$ is C$_{1-4}$ alkyl, C$_{2-4}$ alkenyl, C$_{2-4}$ alkynyl, a group OCOR$_9$—.

Signed and Sealed this

First Day of February, 1994

Attest:

BRUCE LEHMAN

Attesting Officer        Commissioner of Patents and Trademarks

UNITED STATES PATENT AND TRADEMARK OFFICE
CERTIFICATE OF CORRECTION

PATENT NO. : 5,157,160
DATED : Oct. 20, 1992
INVENTOR(S) : Paul A. Wyman

It is certified that error appears in the above-identified patent and that said Letters Patent is hereby corrected as shown below:

Col. 25, claim 1, lines 3-4 (counting the formula as one line), delete the phrase "wherein Z" is a group convertible to Z as defined in claim 12, and".

Signed and Sealed this

Eleventh Day of April, 1995

Attest:

Attesting Officer

BRUCE LEHMAN
Commissioner of Patents and Trademarks